(12) United States Patent
DeHennis et al.

(10) Patent No.: US 11,058,330 B2
(45) Date of Patent: *Jul. 13, 2021

(54) ANALYTE SENSOR

(71) Applicant: Senseonics, Incorporated, Germantown, MD (US)

(72) Inventors: Andrew DeHennis, Germantown, MD (US); Szymon Tankiewicz, Germantown, MD (US); Todd Whitehurst, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 580 days.

This patent is subject to a terminal disclaimer.

(21) Appl. No.: 15/904,940

(22) Filed: Feb. 26, 2018

(65) Prior Publication Data

US 2018/0184953 A1    Jul. 5, 2018

Related U.S. Application Data

(62) Division of application No. 14/629,943, filed on Feb. 24, 2015, now Pat. No. 9,901,293.

(51) Int. Cl.
| | | |
|---|---|---|
| *A61B 5/145* | (2006.01) | |
| *A61B 5/1459* | (2006.01) | |
| *A61B 5/00* | (2006.01) | |

(52) U.S. Cl.
CPC ........ *A61B 5/14532* (2013.01); *A61B 5/0002* (2013.01); *A61B 5/0075* (2013.01); *A61B 5/1459* (2013.01); *A61B 2560/0214* (2013.01)

(58) Field of Classification Search
CPC ... A61B 5/0059; A61B 5/0205; A61B 5/1455; A61B 5/14551; A61B 5/14552;
(Continued)

(56) References Cited

U.S. PATENT DOCUMENTS

| 3,744,044 A | 7/1973 | Vosteen |
|---|---|---|
| 4,703,756 A | 11/1987 | Gough et al. |

(Continued)

FOREIGN PATENT DOCUMENTS

| CN | 101855777 A | 10/2010 |
|---|---|---|
| EP | 0 834 734 A2 | 4/1998 |

(Continued)

OTHER PUBLICATIONS

Abbott, "FreeStyle Libre Flash Glucose Monitoring System User's Manual", 124 pages (2014).

*Primary Examiner* — Chu Chuan Liu
(74) *Attorney, Agent, or Firm* — Rothwell, Figg, Ernst & Manbeck, P.C.

(57) ABSTRACT

Sensors and methods for measurement of an analyte in a medium within a living animal are described. The sensor may include an inductive element that may receive power from an external device. The sensor may also include a charge storage device (CSD) and a memory. The sensor may perform analyte measurements initiated by the external device using power received from the external device and convey the analyte measurements to the external device using the inductive element. The sensor also may perform autonomous analyte measurements using the on board charge device's power and store the autonomous analyte measurements in the memory. The sensor may convey one or more stored analyte measurements to the external device using the inductive element using power received from the external device. The sensor may include a CSD-powered clock and a CSD-powered measurement scheduler that initiate the autonomous analyte measurements.

6 Claims, 9 Drawing Sheets

(58) Field of Classification Search
CPC . A61B 5/14532; A61B 5/1459; A61B 5/1468; A61B 5/14735; A61B 5/1477; A61B 5/1486; A61B 5/14865; A61B 5/1473
See application file for complete search history.

(56) References Cited

U.S. PATENT DOCUMENTS

| | | | |
|---|---|---|---|
| 6,164,284 A * | 12/2000 | Schulman | A61B 5/0031 128/899 |
| 6,185,452 B1 | 2/2001 | Schulman et al. | |
| 6,330,464 B1 | 12/2001 | Colvin, Jr. et al. | |
| 6,400,974 B1 | 6/2002 | Lesho | |
| 6,445,141 B1 | 9/2002 | Kastner et al. | |
| 6,546,268 B1 | 4/2003 | Ishikawa et al. | |
| 7,375,347 B2 | 5/2008 | Colvin, Jr. et al. | |
| 7,831,310 B2 | 11/2010 | Lebel et al. | |
| 8,233,953 B2 | 7/2012 | Colvin, Jr. | |
| 2007/0059196 A1 | 3/2007 | Brister et al. | |
| 2008/0009689 A1 | 1/2008 | Benaron et al. | |
| 2009/0062633 A1 | 3/2009 | Brauker et al. | |
| 2009/0079656 A1 | 3/2009 | Peyla et al. | |
| 2009/0240120 A1 | 9/2009 | Mensinger et al. | |
| 2011/0196213 A1 * | 8/2011 | Thukral | A61B 5/7275 600/301 |
| 2011/0213225 A1 | 9/2011 | Bernstein et al. | |
| 2012/0101874 A1 | 4/2012 | Ben-Haim et al. | |
| 2013/0241745 A1 | 9/2013 | Colvin, Jr. et al. | |
| 2013/0261703 A1 | 10/2013 | Chow et al. | |
| 2013/0296670 A1 | 11/2013 | Chen et al. | |
| 2013/0328572 A1 | 12/2013 | Wang et al. | |
| 2013/0331667 A1 | 12/2013 | Colvin, Jr. et al. | |
| 2014/0378791 A1 | 12/2014 | DeHennis et al. | |
| 2015/0127738 A1 | 5/2015 | Thompson et al. | |
| 2018/0168438 A1 | 6/2018 | Gazdzinski | |

FOREIGN PATENT DOCUMENTS

| | | |
|---|---|---|
| EP | 1 956 365 B1 | 1/2013 |
| EP | 2581887 A1 | 4/2013 |
| WO | 02/062215 A2 | 8/2002 |
| WO | 2013/119951 A2 | 8/2013 |

* cited by examiner

ANALYTE SENSOR

CROSS-REFERENCE TO RELATED APPLICATION

The present application is a divisional of U.S. patent application Ser. No. 14/629,943, filed on Feb. 24, 2015, which is incorporated by reference in its entirety.

BACKGROUND

Field of the Invention

The present invention relates to a sensor for obtaining analyte measurements. Specifically, the present invention relates to an implantable sensor and methods of using the same that improve analyte sensor measurement.

Discussion of the Background

An implantable sensor that has no charge storage device may rely exclusively on an external device for operational power (e.g., to operate its circuitry for making measurements and conveying the data to the external device). The sensor and the external device may each include an inductive element (e.g., coil). The sensor may receive power from the external device when the external device uses its inductive element to generate an electrodynamic field and the inductive elements of the sensor and external device are magnetically coupled within the electrodynamic field. However, with no internal power source, the sensor is dormant if the sensor is not located in the proximity of the external device (i.e., if the inductive elements of the sensor and the external device are not coupled within the electrodynamic field generated by the external device).

For instance, the sensor having no charge storage device may be implanted in the arm of a human patient, and the sensor may be located in the proximity of the external device when the human patient wears an armband having the external device therein. The sensor would be able to take analyte measurements and convey data to the external device while the patient is wearing the armband, but the sensor would not be able to able to take analyte measurements while the patient was not wearing the armband (e.g., because the human patient is swimming or showering), and the result would be a gap in analyte measurement information.

Accordingly, there is a need for an improved sensor and methods for using the same that improve the ability of the sensor to take analyte measurements.

SUMMARY

One aspect of the invention may provide a sensor for implantation within a living animal and measurement of an analyte in a medium within the living animal. The sensor may include an analyte indicator, sensor elements, an inductive element, an input/output circuit, a measurement controller, and a charge storage device. The analyte indicator may be configured to exhibit a detectable property based on the amount or concentration of the analyte in the medium. The sensor elements may be configured to generate an analyte measurement signal based on the detectable property exhibited by the analyte indicator. The inductive element may be configured to produce a current when in an electrodynamic field generated by an external device. The input/output circuit may be configured to wirelessly convey measurement information to the external device via the inductive element. The measurement controller may be configured to (i) control the sensor elements to generate a first analyte measurement signal using power provided by the charge storage device while the inductive element is not in an electrodynamic field generated by the external device; (ii) generate first measurement information based on the first analyte measurement signal; and (iii) control the input/output circuit to wirelessly convey the first measurement information to the external device while the inductive element is in an electrodynamic field generated by the external device.

In some embodiments, the sensor may include a nonvolatile storage medium. In some embodiments, the measurement controller may be further configured to store the first measurement information in the nonvolatile storage medium. In some embodiments, the measurement controller may be further configured to: control the sensor elements to generate a second analyte measurement signal using the power provided by the charge storage device while the inductive element is not in an electrodynamic field generated by the external device; generate second measurement information based on the second analyte measurement signal; store the second measurement information in the nonvolatile storage medium; and control the input/output circuit to wirelessly convey the second measurement information to the external device while the inductive element is in an electrodynamic field generated by the external device.

In some embodiments, the measurement controller may be further configured to: control the sensor elements to generate a second analyte measurement signal while the inductive element is in an electrodynamic field generated by the external device; generate second measurement information based on the second analyte measurement signal; and control the input/output circuit to wirelessly convey the second measurement information to the external device while the inductive element is in an electrodynamic field generated by the external device.

In some embodiments, the sensor may include a clock that is powered by the charge storage device. In some embodiments, the clock may be a low-power oscillator, real time clock. In some embodiments, the sensor may include a measurement scheduler that is powered by the charge storage device and configured to issue a first autonomous measurement command based on an output of the clock, and the measurement controller may be configured to control the sensor elements to generate the first analyte measurement signal in response to the first autonomous measurement command. In some embodiments, the measurement scheduler may be configured to issue autonomous measurement commands at periodic intervals based on the output of the clock. In some embodiments, the sensor may include a power switch configured to switch one or more of the sensor elements, the input/output circuit, and the measurement controller from being powered by externally supplied power to being powered by the charge storage device in response to the first autonomous measurement command.

In some embodiments, the input/output circuit may include: a capacitor; and a tuning capacitor bank configured to dynamically tune an LC tank circuit comprising the inductive element and the capacitor and to change a resonant frequency of the LC tank circuit. In some embodiments, the tuning capacitor bank may include a varactor diode. In some embodiments, the input/output circuit may include an over-temperature protection circuit configured to control the tuning capacitor bank to detune the LC tank circuit so as to reduce power delivered by the LC tank circuit in the case of overheating of the sensor.

In some embodiments, the detectable property exhibited by the analyte indicator may be an optical characteristic responsive to the amount or concentration of the analyte in the medium, and the sensor elements may include: a first photodetector configured to output an analog light measurement signal indicative of the amount of light received by the first photodetector; and a first light source configured to emit first excitation light to the analyte indicator. In some embodiments, the sensor elements may further include a second light source configured to emit second excitation light to the analyte indicator, and the first and second excitation lights may have different wavelengths. In some embodiments, the sensor elements may further include a second photodetector configured to output an analog light measurement signal indicative of the amount of light received by the second photodetector. In some embodiments, the sensor may include: a first optical filter configured to cover a photosensitive side of the first photodetector and to allow light having a first wavelength to pass through; and a second optical filter configured to cover a photosensitive side of the second photodetector and to allow light having a second wavelength to pass through, and the first and second wavelengths may be different. In some embodiments, the first and second optical filters may be coated on the photosensitive sides of the first and second photodetectors, respectively. In some embodiments, the sensor may include a semiconductor substrate, and the first photodetector may be fabricated in the semiconductor substrate.

In some embodiments, the input/output circuit may include: a rectifier configured to convert an alternating current produced by the inductive element while the inductive element is in an electrodynamic field generated by the external device to a direct current; and a charger configured to recharge the charge storage device using the direct current generated by the rectifier. In some embodiments, the sensor elements may include: photodetectors symmetrically arranged on either side of a center line running between the photodetectors; and light sources having emission points on the center line. In some embodiments, the first measurement information may include a time-stamp identifying the time at which the first measurement information was generated. In some embodiments, the sensor may include an analog to digital converter (ADC) configured to convert an analog analyte measurement signal to a digital analyte measurement signal.

In some embodiments, the sensor elements may include: a first temperature transducer configured to output a first analog temperature measurement signal indicative of a temperature of the sensor; and a second temperature transducer configured to output a second analog temperature measurement signal indicative of the temperature of the sensor. In some embodiments, the inductive element may be a coil. In some embodiments, the charge storage device and semiconductor substrate may be located within the coil.

In some embodiments, the medium may be interstitial, intravascular, or intraperitoneal fluid. In some embodiments, the analyte may be glucose. In some embodiments, the input/output circuit may include a monitor configured to detect whether the voltage of the charge storage device is above or below a threshold.

Another aspect of the invention may provide a method of using a sensor to measure an analyte in a medium within a living animal. The method may include controlling the sensor elements of the sensor to generate a first analyte measurement signal using power provided by a charge storage device of the sensor while an inductive element of the sensor is not in an electrodynamic field generated by an external device. The sensor elements may be configured to generate the first analyte measurement signal based on a detectable property exhibited by an analyte indicator of the sensor, and the analyte indicator may be configured to exhibit the detectable property based on the amount or concentration of the analyte in the medium. The method may include generating first measurement information based on the first analyte measurement signal. The method may include controlling an input/output circuit of the sensor to wirelessly convey the first measurement information to the external device via the inductive element while the inductive element is in an electrodynamic field generated by the external device.

In some embodiments, method may include: storing the first measurement information in a nonvolatile storage medium of the sensor; controlling the sensor elements to generate a second analyte measurement signal using power provided by the charge storage device while the inductive element is not in an electrodynamic field generated by the external device; generating second measurement information based on the second analyte measurement signal; and controlling the input/output circuit of the sensor to wirelessly convey the stored second measurement information to the external device via the inductive element while the inductive element is in an electrodynamic field generated by the external device. In some embodiments, the method may include: issuing an autonomous measurement command based on the output of a clock that is powered by the charge storage device; and switching the sensor elements from being powered by externally supplied power to being powered by the charge storage device in response to the autonomous measurement command.

Another aspect of the invention may provide a sensor for implantation within a living animal and measurement of an analyte in a medium within the living animal. The sensor may include: an analyte indicator, sensor elements, a measurement controller, a non-volatile storage medium, a charge storage device, and a measurement scheduler. The analyte indicator may be configured to exhibit a detectable property based on the amount or concentration of the analyte in the medium. The sensor elements may be configured to generate an analyte measurement signal based on the detectable property exhibited by the analyte indicator. The measurement scheduler may be powered by the charge storage device and is configured to issue an autonomous measurement command. The measurement controller may be configured to: (i) control the sensor elements to generate a first analyte measurement signal using power provided by the charge storage device in response to the autonomous measurement command; (ii) generate first measurement information based on the first analyte measurement signal; and (iii) store the first measurement information in the non-volatile storage medium.

In some embodiments, the sensor may include a clock that is powered by the charge storage device, and the measurement scheduler may be configured to use an output of the clock to determine when to issue the measurement command. In some embodiments, the sensor may include a power switch configured to switch one or more of the sensor elements and the measurement controller from being powered by the external device to being powered by the charge storage device in response to the autonomous measurement command.

Another aspect of the invention may provide a method of using a sensor to measure an analyte in a medium within a living animal. The method may include using a charge storage device of the sensor to power a measurement scheduler. The method may include using the measurement scheduler to issue an autonomous measurement command. The method may include controlling sensor elements of the sensor to generate a first analyte measurement signal using power provided by the charge storage device in response to the autonomous measurement command. The first analyte measurement signal may be based on a detectable property exhibited by an analyte indicator of the sensor, and the analyte indicator may be configured to exhibit the detectable property based on the amount or concentration of the analyte in the medium. The method may include generating first measurement information based on the first analyte measurement signal. The method may include storing the first measurement information in a non-volatile storage medium of the sensor.

In some embodiments, the method may include using the charge storage device to power a clock. Using the measurement scheduler to issue an autonomous measurement command may include using an output of the clock to determine when to issue the measurement command. In some embodiments, the method may include switching sensor elements of the sensor from being powered by an external device to being powered by the charge storage device in response to the autonomous measurement command.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

DETAILED DESCRIPTION OF THE PREFERRED EMBODIMENTS

Figure 1:
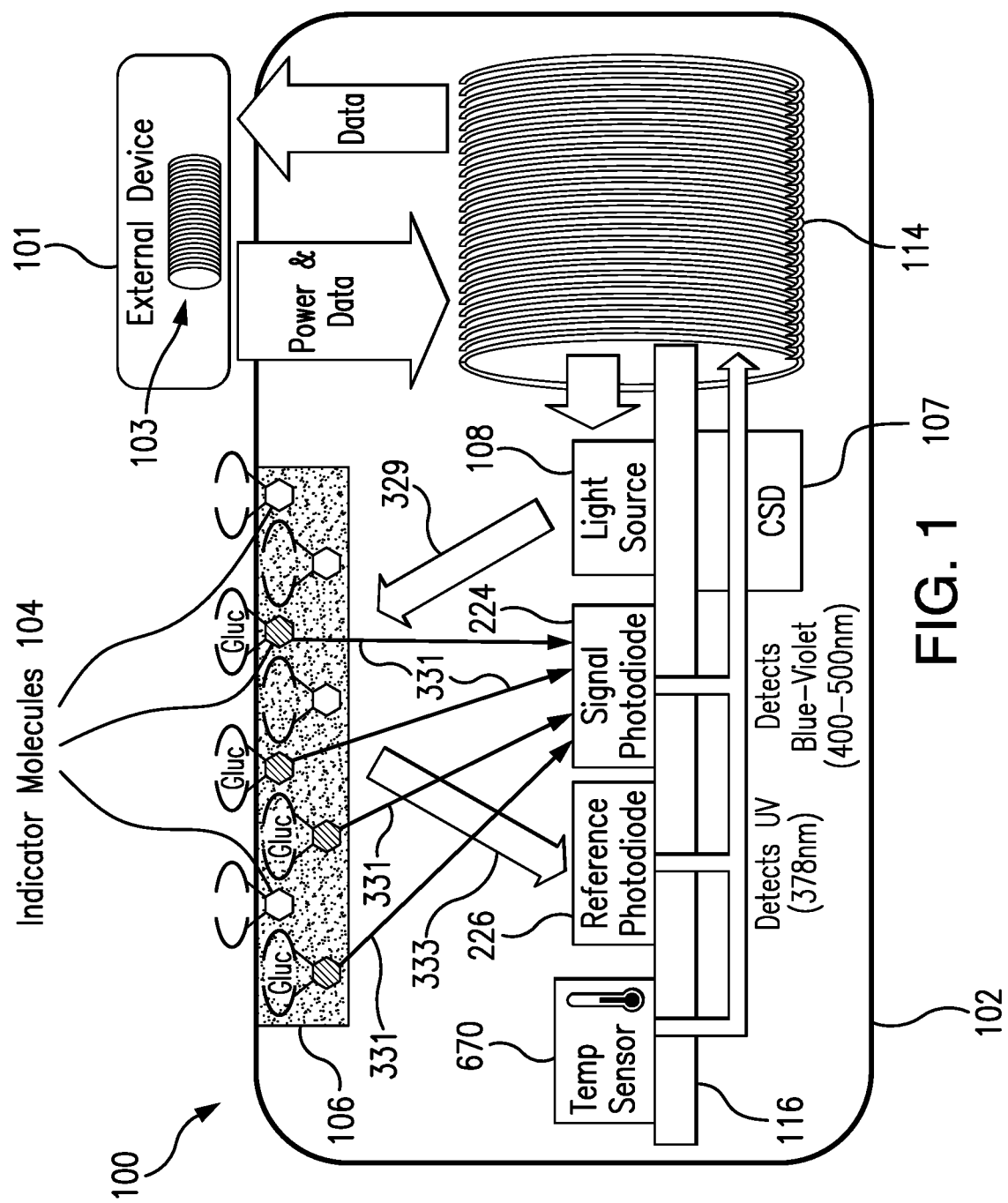
FIG. 1 is a schematic view of an analyte monitoring system embodying aspects of the present invention.

FIG. 1 is a schematic view of an analyte monitoring system embodying aspects of the present invention. As illustrated in FIG. 1, the system may include an analyte sensor 100 and an external device 101. In some non-limiting embodiments, the sensor 100 may be a fully implantable analyte sensor. The sensor 100 may be implanted in a living animal (e.g., a living human). The sensor 100 may be implanted, for example, in a living animal's arm, wrist, leg, abdomen, peritoneum, intravenously, or other region of the living animal suitable for sensor implantation. For example, in one non-limiting embodiment, the sensor 100 may be implanted beneath the skin (i.e., in the subcutaneous or peritoneal tissues). The sensor 100 may be configured to measure an analyte (e.g., glucose, oxygen, cardiac markers, low-density lipoprotein (LDL), high-density lipoprotein (HDL), or triglycerides) in a medium (e.g., interstitial, intravascular, or intraperitoneal fluids) within the living animal.

The external device 101 may be an electronic device (e.g., a dedicated medical device, transceiver, transmitter, smartphone, personal data assistant, tablet computer, or other handheld communication device) that communicates with the sensor 100 to provide power to the sensor 100 and/or receive measurement information (e.g., photodetector and/or temperature sensor readings) from the sensor 100. In some non-limiting embodiments, the external device 101 may be a handheld device or an on-body/wearable device. For example, in some embodiments where the external device 101 is an on-body/wearable device, the external device 101 may be held in place by a band (e.g., an armband or wristband) and/or adhesive (e.g., as part of a biocompatible patch), and the external device 101 may convey (e.g., periodically, such as every two minutes, and/or upon user initiation) measurement commands (i.e., requests for measurement information) to the sensor 100. In some embodiments where the external device 101 is a handheld device, positioning (i.e., hovering or swiping/waving/passing) the external device 101 within range over the sensor implant site (i.e., within proximity of the sensor 100) may cause the external device 101 to automatically convey a measurement command to the sensor 100 and receive a reading from the sensor 100. In some embodiments, the external device 101 may implement a passive telemetry for communicating with the implantable sensor 100 via an inductive magnetic link for power and/or data transfer.

In some embodiments, as illustrated in FIG. 1, the external device 101 may include an inductive element 103, and the sensor 100 may include an inductive element 114. In some non-limiting embodiments, the inductive elements 103 and 114 may be, for example, coils. The inductive element 103 of the external device 101 and the inductive element 114 of the sensor 100 may be in any configuration that permits adequate field strength to be achieved when the two inductive elements are brought within adequate physical proximity.

The external device 101 may generate an electromagnetic wave or electrodynamic field (e.g., by using the inductive element 103) to induce a current in the inductive element 114 of the sensor 100, which may be used to power the sensor 100. The external device 101 may also convey data (e.g., commands) to the sensor 100. For example, in a non-limiting embodiment, the external device 101 may convey data by modulating the electromagnetic wave used to power the sensor 100 (e.g., by modulating the current flowing through a coil 103 of the external device 101). The modulation in the electromagnetic wave generated by the external device 101 may be detected/extracted by the sensor 100. Moreover, the external device 101 may receive data (e.g., measurement information) from the sensor 100. For example, in a non-limiting embodiment, the external device 101 may receive data by detecting modulations in the electromagnetic wave generated by the sensor 100, e.g., by detecting modulations in the current flowing through the coil 103 of the external device 101.

In some embodiments, the magnetic external device-sensor link can be considered a "weakly coupled transformer" type. In some embodiments, the magnetic external device-sensor link may provide energy and/or a link for data transfer using amplitude modulation (AM). Although in some embodiments, data transfer is carried out using AM, in alternative embodiments, other types of modulation may be used. In some non-limiting embodiments, the analyte monitoring system may use a frequency of 13.56 MHz, which can achieve high penetration through the skin and is a medically approved frequency band, for power transfer. However, this is not required, and, in other embodiments, different frequencies may be used for providing power to and/or communicating with the sensor 100.

In some non-limiting embodiments, as illustrated in FIG. 1, the sensor 100 may be encased in a sensor housing 102 (i.e., body, shell, capsule, or encasement), which may be rigid and biocompatible. The sensor 100 may include one or more analyte indicators 106, which may be, for example, a polymer graft coated, diffused, adhered, or embedded on or in at least a portion of the exterior surface of the sensor housing 102. The one or more analyte indicator 106 (e.g., polymer graft) of the sensor 100 may include indicator molecules 104 (e.g., fluorescent indicator molecules) exhibiting one or more detectable properties (e.g., optical properties) based on the amount or concentration of the analyte in proximity to the analyte indicator element.

In some embodiments, the sensor 100 may include sensor elements. In some non-limiting embodiments, the sensor elements may include one or more light sources 108, one or more photodetectors 224, 226, and/or one or more temperature transducers 670. In some embodiments, the one or more light source 108 may emit excitation light 329 over a range of wavelengths that interact with the indicator molecules 104. In some embodiments, the one or more photodetectors 224, 226 (e.g., photodiodes, phototransistors, photoresistors, or other photosensitive elements) may generate a measurement signal that is indicative of the amount of light received by the photodetectors. One or more of the photodetectors (e.g., photodetector 224) may be sensitive to emission light 331 (e.g., fluorescent light) emitted by the indicator molecules 104 such that a signal generated by the photodetector (e.g., photodetector 224) in response thereto that is indicative of the level of emission light 331 of the indicator molecules and, thus, the amount of analyte of interest (e.g., glucose). In some non-limiting embodiments, one or more of the photodetectors (e.g., photodetector 226) may be sensitive to excitation light 329 that is reflected from the analyte indicator element 106 as reflection light 333. In some non-limiting embodiments, one or more of the photodetectors may be covered by one or more filters that allow only a certain subset of wavelengths of light to pass through (e.g., a subset of wavelengths corresponding to emission light 331 or a subset of wavelengths corresponding to reflection light 333) and reflect the remaining wavelengths.

In some embodiments, as illustrated in FIG. 1, the sensor 100 may include a substrate 116. In some embodiments, the substrate 116 may be a circuit board (e.g., a printed circuit board (PCB) or flexible PCB) on which circuit components (e.g., analog and/or digital circuit components) may be mounted or otherwise attached. However, in some alternative embodiments, the substrate 116 may be a semiconductor substrate having circuitry fabricated therein (e.g., using a complimentary metal oxide semiconductor (CMOS) process, an n-type metal-oxide-semiconductor (NMOS) process, or a p-type metal-oxide-semiconductor (PMOS) process). The circuitry may include analog and/or digital circuitry. Also, in some semiconductor substrate embodiments, in addition to the circuitry fabricated in the semiconductor substrate, circuitry may be mounted or otherwise attached to the semiconductor substrate 116. In other words, in some semiconductor substrate embodiments, a portion or all of the circuitry, which may include discrete circuit elements, an integrated circuit (e.g., an application specific integrated circuit (ASIC)) and/or other electronic components (e.g., a non-volatile memory), may be fabricated in the semiconductor substrate 116 with the remainder of the circuitry is secured to the semiconductor substrate 116, which may provide communication paths between the various secured components.

In some embodiments, one or more of the sensor housing 102, analyte indicator element 106, indicator molecules 104, light source 108, photodetectors 224, 226, temperature transducer 670, substrate 116, and inductive element 114 of sensor 100 may include some or all of the features described in one or more of U.S. Patent Application Publication Nos. 2013/0211213, 2014/0018644, and 2013/0241745, all of which are incorporated by reference in their entireties. Similarly, the structure and/or function of the sensor 100 and/or external device 101 may be as described in one or more of U.S. Patent Application Publication Nos. 2013/0211213, 2014/0018644, and 2013/0241745.

Although in some embodiments, as illustrated in FIG. 1, the sensor 100 may be an optical sensor, this is not required, and, in one or more alternative embodiments, sensor 100 may be a different type of analyte sensor, such as, for example, a diffusion sensor or a pressure sensor.

In some embodiments, the sensor 100 may include a charge storage device (CSD) 107. In some embodiments, the charge storage device 107 may be a rechargeable battery (e.g., a lithium-ion battery). In some embodiments, the charge storage device 107 may be, for example, a battery or a capacitor or a super capacitor. In some non-limiting embodiments, the charge storage device 107 may last for a year or more, depending on total number of recharge cycles (e.g., the battery 107 may drop to 80% of its initial capacity after 500 recharge cycles). In some non-limiting embodiments, the charge storage device 107 may have enough capacity to power the sensor 100 over desired period of time (e.g., one day, one week, one month, three months, six months, twelve months, or more). In some embodiments, the charge storage device 107 may power the sensor 100 (e.g., when the sensor 100 is not receiving power from the external device 101). In some embodiments, using power supplied by the charge storage device 107, the sensor 100 may operate autonomously and take one or more analyte measurements when the inductive element 114 of the sensor 100 is not coupled with the inductive element 103 of an external device 101 in an electrodynamic field generated by the external device (i.e., even when the inductive element 114 of the sensor 100 is not co-located with the inductive element 103 of an external device 101). In some embodiments, the sensor 100 may store one or more autonomous analyte measurements in a memory within the sensor, and the sensor 100 may convey one or more of the stored measurements to the external device 101 at a later time when the inductive elements 114 and 103 of the sensor 100 and external device 101 are coupled.

Figure 2A:
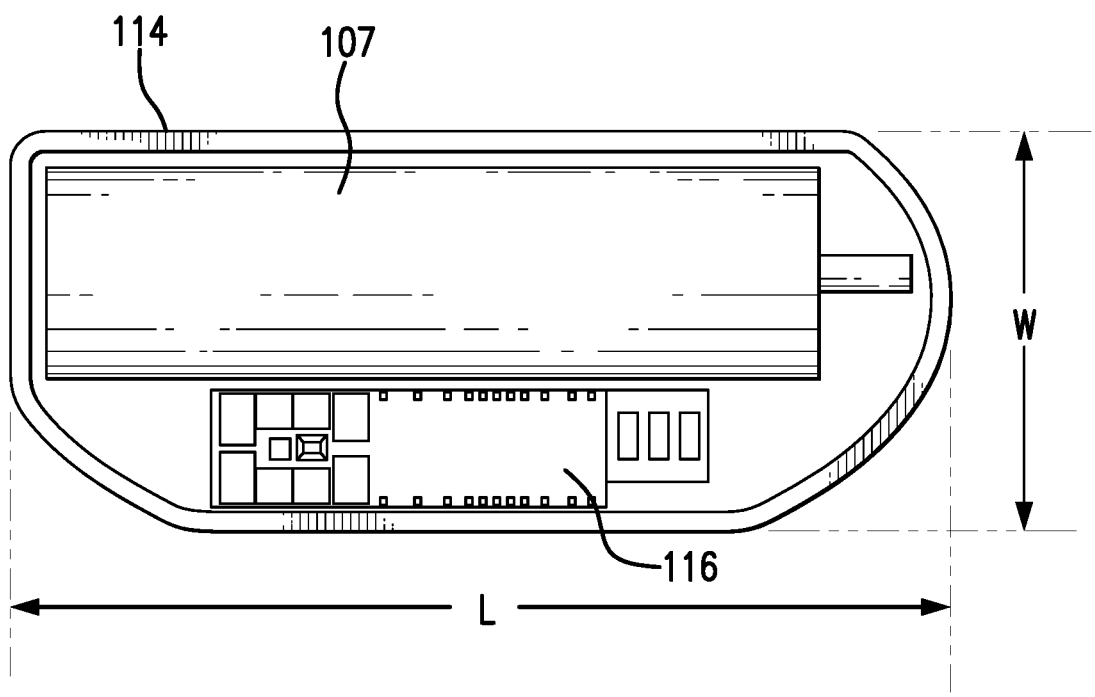
FIGS. 2A-2C illustrate top, side, and perspective views, respectively, of an inductive element, substrate, and charge storage device configuration embodying aspects of the present invention.
Figure 2B:
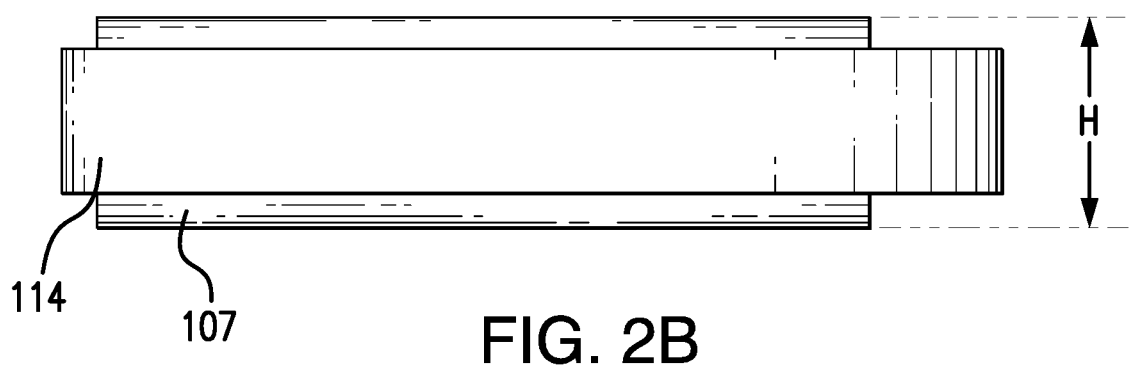
Figure 2C:
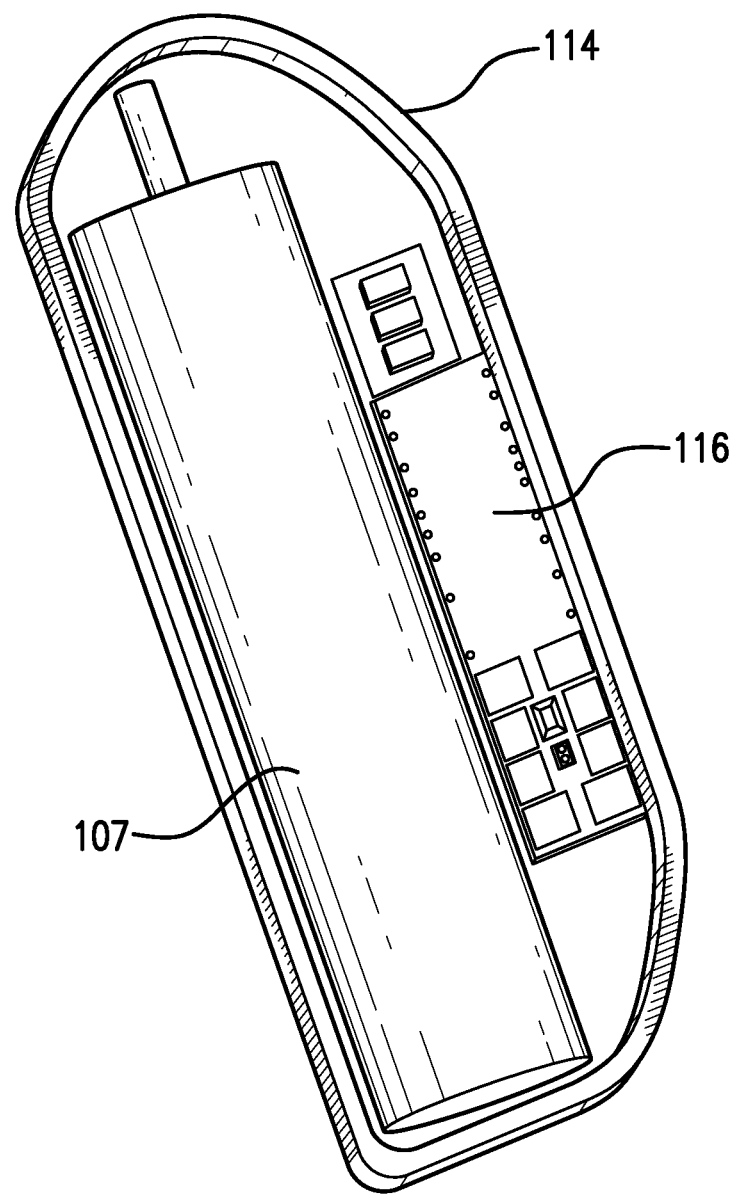

In some non-limiting embodiments, the inductive element 114, substrate 116, and battery 107 of the sensor 100 may be arranged within the sensor housing 102 as illustrated in FIGS. 2A, 2B, and 2C, which show top, side, and perspective views, respectively, of the inductive element 114, substrate 116, and charge storage device 107 configuration. In some non-limiting embodiments, as shown in FIGS. 2A-2C, the inductive element 114 may be configured as a coil (e.g., a planar or spiral coil), and the substrate 116 and charge storage device 107 may be located side-by-side within the coil. In some embodiments, as shown in FIGS. 2A and 2C, the inductive element 114 may be shaped so as to accommodate the shape of the side-by-side substrate 116 and charge storage device 107. In some non-limiting embodiments, as shown in FIGS. 2A and 2B, the inductive element 114, substrate 116, and charge storage device 107 configuration may have an overall length, width, and height of 0.56, 0.22, and 0.11 inches, respectively. However, this is not required, and, in some embodiments, the inductive element 114, substrate 116, and charge storage device 107 configuration may have different overall dimensions. The inductive element 114, substrate 116, and charge storage device 107 configuration may be encased within the sensor housing 102, and the one or more light sources 108 mounted on or fabricated in the substrate 116 may be configured to emit excitation light 329 to one or more one or more analyte indicators 106 on or in at least a portion of the exterior surface of the sensor housing 102 (see, for example, FIG. 1).

Figure 3:
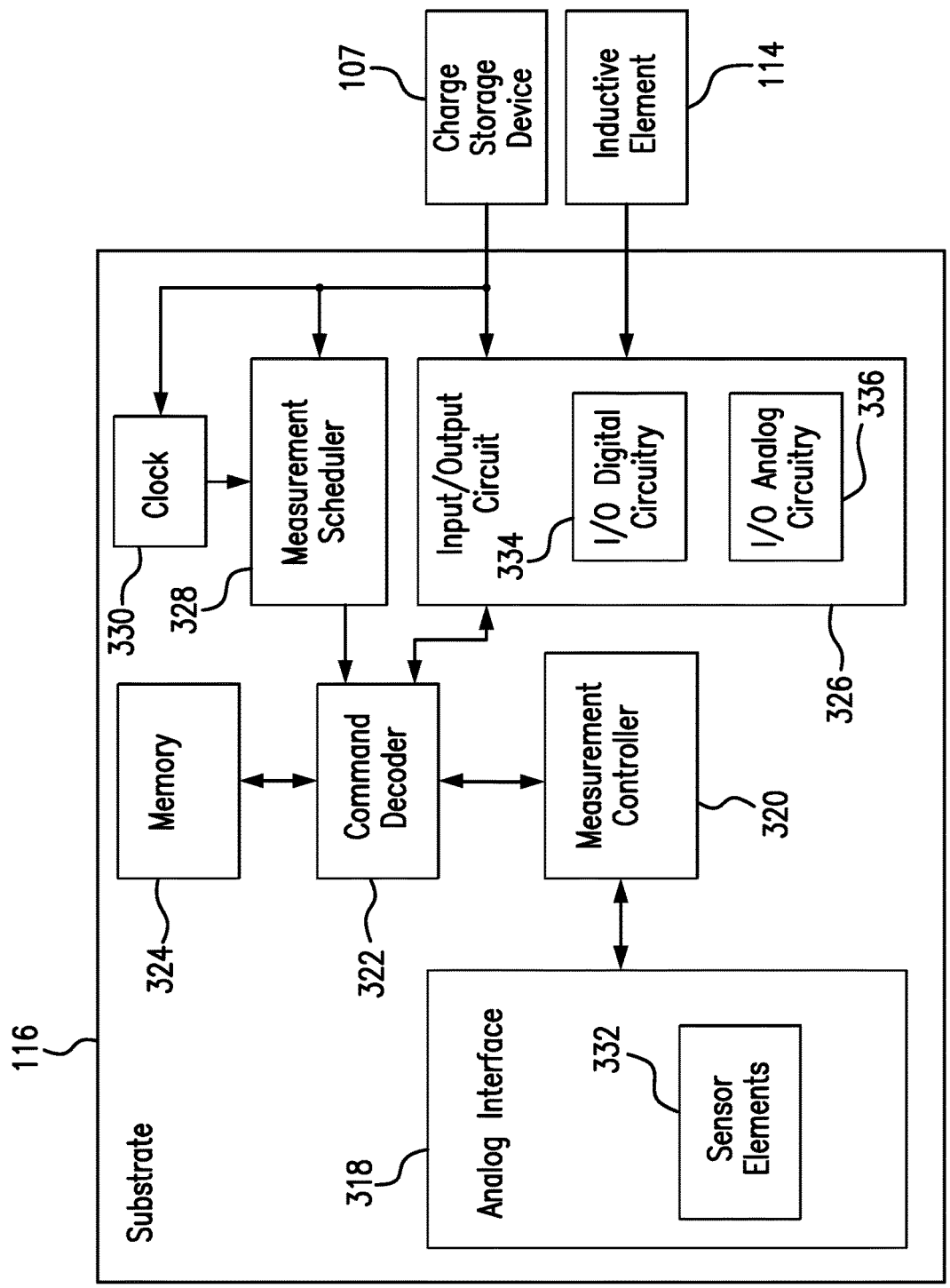
FIG. 3 is a block diagram illustrating the main functional blocks of the circuitry of an analyte sensor embodying aspects of the present invention.

FIG. 3 is a block diagram illustrating the main functional blocks of the circuitry of an analyte sensor embodying aspects of the present invention. In some embodiments, as illustrated in FIG. 3, the circuitry mounted on or fabricated in the substrate 116 of the sensor 100 may include one or more of an analog interface 318, a measurement controller 320, a command decoder 322, a memory 324, an input/output (I/O) circuit 326, a measurement scheduler 328, and a clock 330. In some embodiments, the analog interface 318 may include one or more sensor elements 332 mounted on or fabricated in the substrate 116. In some embodiments, the sensor 100 may alternatively or additionally have one or more sensor elements external to the substrate 116 (i.e., sensor elements that that are neither mounted on nor fabricated in the substrate 166) but electrically connected to the analog interface 318 via one or more contacts.

In some embodiments, the I/O circuit 326 may include I/O digital circuitry 334 and/or I/O analog circuitry 336. In some embodiments, the inductive element 114 may be electrically connected to the I/O circuit 326, which may use current flowing through the inductive element 114 to generate power for the sensor 100 and to extract data therefrom. The I/O circuit 326 may also convey data (e.g., to an external device 101) by modulating the current the flowing through the inductive element 114. In some embodiments, the I/O circuit 326 may be electrically connected to the charge storage device 107 and may use the charge storage device 107 to power the sensor 100 (e.g., at times when the sensor 100 is not receiving power from an external device 101).

In some embodiments, the charge storage device (CSD) 107 may provide power to the clock 330 and to the measurement scheduler 328. The CSD-powered clock 330 may provide a continuous clock for driving circuitry of the sensor 100 even when the sensor 100 is not receiving power from an external device 101. The measurement scheduler 328 may use the continuous clock output of the clock 330 to keep track of time and initiate autonomous, self-powered analyte measurements when appropriate (e.g., at periodic intervals, such as, for example, every minute, every two minutes, every 5 minutes, every 10 minutes, every half-hour, every hour, every two hours, every six hours, every twelve hours, or every day). The autonomous analyte measurements may be stored in the memory 324. In some embodiments, the I/O circuit 326 may convey one or more of the stored measurements to the external device 101 at a later time when an external device 101 is present (i.e., when the inductive elements 114 and 103 of the sensor 100 and external device 101 are coupled, and an electrodynamic field generated by the external device 101 induces a current in the inductive element 114 of the sensor 100).

Figure 4A:
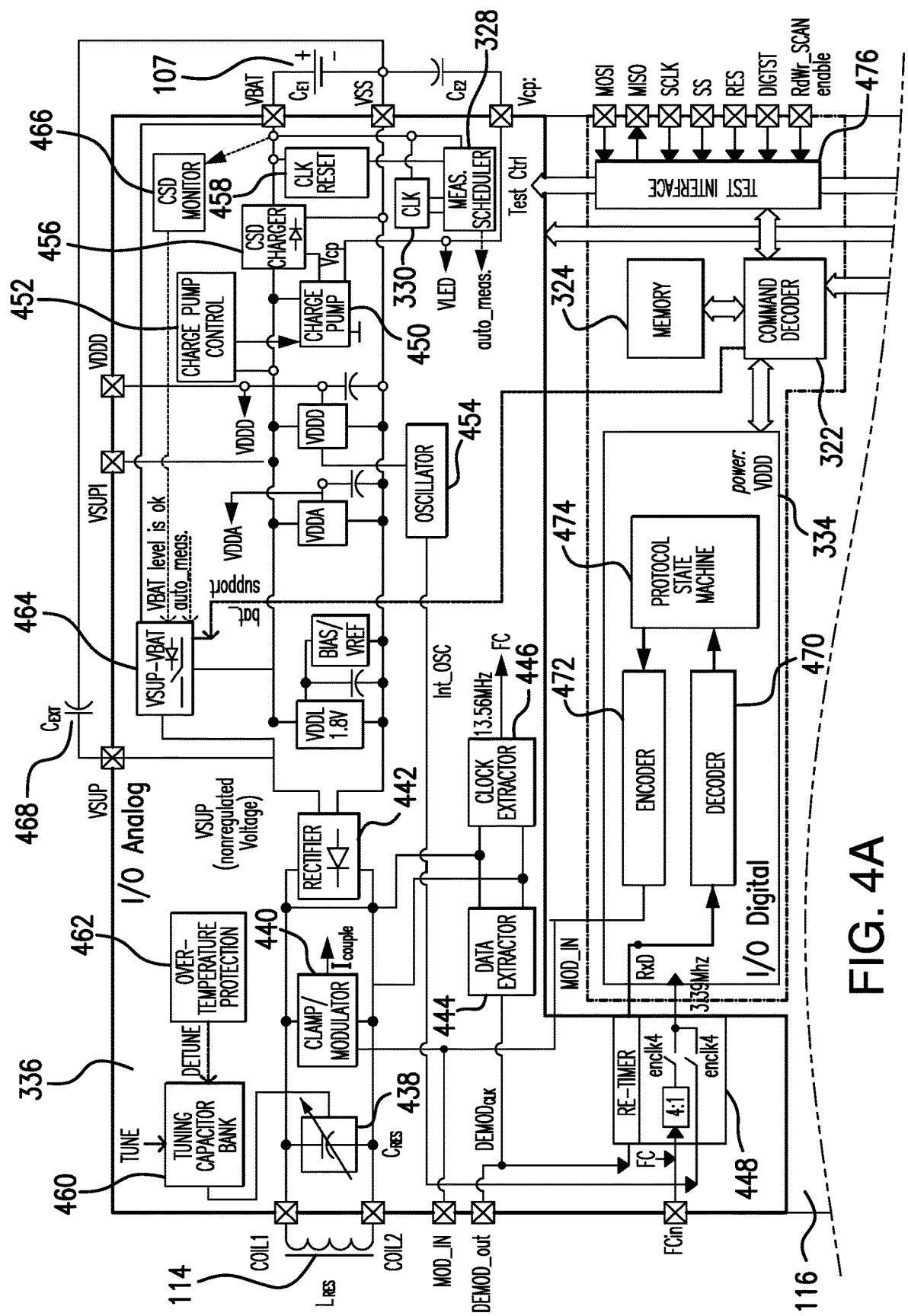
FIGS. 4A and 4B are a block diagram illustrating the functional blocks of circuitry of an analyte sensor embodying aspects of the present invention.
Figure 4B:
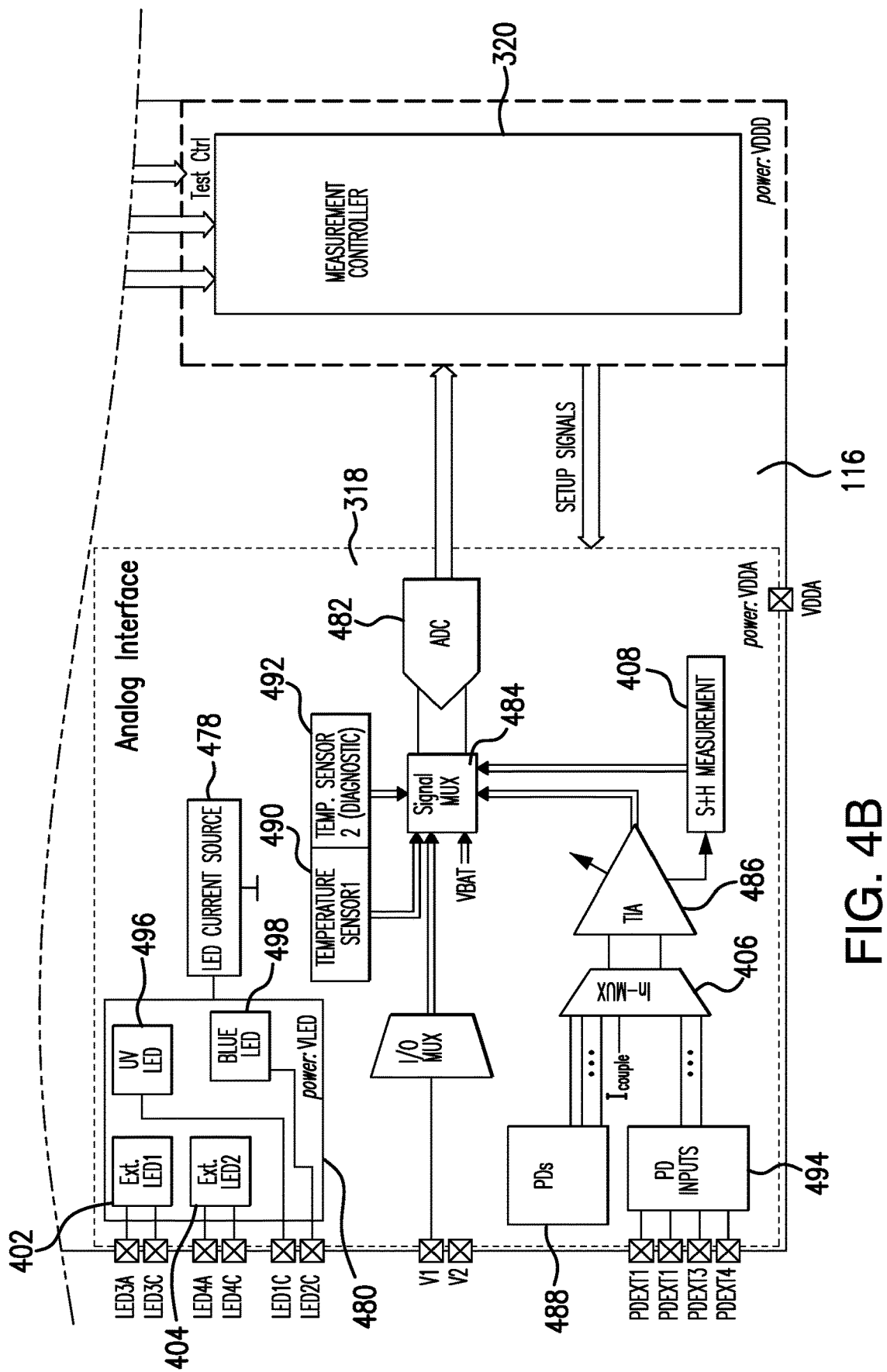

FIGS. 4A and 4B are a block diagram illustrating, in more detail, the functional blocks of circuitry mounted on or fabricated in the substrate 116 according to some embodiments. In some embodiments, as shown in FIG. 4A, the inductive element 114, which may be in the form of a coil, may be external to the substrate 116 and may be connected to the I/O analog circuitry 336 through contacts COIL1 and COIL2. In some embodiments, the I/O analog circuitry 336 may include one or more of a capacitor 438, clamp/modulator 440, a rectifier 442, a data extractor 444, a clock extractor 446, a frequency divider 448, a charge pump 450, a charge pump controller 452, and an oscillator 454. In some embodiments, one or more of the capacitor 438, clamp/modulator 440, rectifier 442, data extractor 444, and clock extractor 446 may be connected to the inductive element 114 through one or more of contacts COIL1 and COIL2. The rectifier 442 may convert an alternating current produced by the inductive element 114 to a direct current that may be used to power the sensor 100. For example, the direct current may be used to produce one or more voltages, such as, for example, voltages VDDA, which may be used to power the analog interface 318, and/or VDDD, which may be used to power one or more of the I/O digital circuit 336, the memory 324, the measurement controller 320, the command decoder 322, the measurement scheduler 318, and a test interface 476. In one non-limiting embodiment, the rectifier 442 may be a Schottky diode; however, other types of rectifiers may be used in some alternative embodiments. In some embodiments, the data extractor 444 may extract data from the alternating current produced by the inductive element 114. In some embodiments, the clock extractor 446 may extract a signal having a frequency (e.g., 13.56 MHz) from the alternating current produced by the inductive element 114. In some embodiments, the frequency divider 448 may divide the frequency of the signal output by the clock extractor 446. For example, in a non-limiting embodiment, the frequency divider 448 may comprise a 4:1 frequency divider that receives a signal having a frequency (e.g., 13.56 MHz) as an input and outputs a signal having a frequency (e.g., 3.39 MHz) equal to one fourth the frequency of the input signal. In some embodiments, the frequency divider 448 may output either the frequency divided output of the clock extractor 446 or the output of the oscillator 454 to the I/O digital circuitry 336. In some embodiments, the outputs of rectifier 442 may be connected to one or more capacitors 468 (e.g., one or more regulation capacitors) through contacts VSUP and VSS.

In some embodiments, as shown in FIG. 4A, the I/O analog circuitry 336 may include one or more of a tuning capacitor bank 460 and an over temperature protection circuit 462. In some embodiments, the tuning capacitor bank 460 may dynamically tune (or detune) an LC tank circuit including the inductive element 114 and the capacitor 438 and thereby change a resonant frequency of the LC tank circuit. In some embodiments, the tuning capacitor bank 460 may change the resonant frequency of the LC tank circuit of the sensor 100 to compensate for detuning of an external device 101, to compensate for detuning of the sensor 100 caused by the environment in which the sensor 100 is placed (e.g., patient-dependent detuning), and/or to change the amount of power delivered to the sensor 100. In some non-limiting embodiments, the tuning capacitor bank 460 may comprise a varactor diode (i.e., voltage controlled capacitor), which may be used to electronically and programmatically change the tuning of the sensor 100 (e.g., to optimize the communications link between the sensor 100 and an external device 101). In some non-limiting embodiments, an over-temperature protection circuit 462 may control the tuning capacitor bank 460 to detune the sensor 100 and, thereby, reduce amount of power delivered to the sensor 100 in the case of excessive heating of the sensor 100 (e.g., overheating during charging of the charge storage device 107).

In some embodiments, as shown in FIG. 4A, the I/O analog circuitry 336 may include one or more of a CSD charger 456, a charge pump 450, and a charge pump controller 452. In some embodiments, the CSD charger 456 may charge and/or recharge the charge storage device 107 using power supplied by an external device 101. In some embodiments, the CSD charger 456 may provide a variable threshold voltage for different charge storage device options. In some non-limiting embodiments, the CSD charger 456 may use a constant current mode of charging to provide fast method of charge storage device charging without sacrificing the capacity and longevity of charge storage device 107. In some embodiments, the charge pump 450 may produce a voltage VLED that is used to power the one or more light sources 108. In some embodiments, the charge pump 450 may additionally or alternatively produce a voltage VCP that is used by the CSD charger 456 to charge the charge storage device 107. In some embodiments, the charge pump controller 452 may control whether the charge pump 450 produces the voltage VCP used to charge the charge storage device 107. In some embodiments, control by the charge pump controller 452 may be dependent on the voltage VSUP, which is the voltage supplied to the sensor 100 via the inductive element 114 and rectifier 442. For instance, in some non-limiting embodiments, the charge pump controller 452 may control the charge pump to only produce the voltage VCP used to charge the charge storage device 107 only when an external device 101 is supplying power to the sensor 100 by inducing a current in the inductive element 114, which the I/O analog circuitry 336 of the sensor 100 uses to generate the voltage VSUP.

In some embodiments, the I/O analog circuitry 336 may include a clock controller 458. The clock controller 458 may reset the measurement scheduler 328.

In some embodiments, as shown in FIG. 4A, the I/O analog circuitry 336 may include a power switch 464. The power switch 464 may switch the sensor 100 between CSD power provided by the charge storage device 107 and externally supplied power provided by an external device 101 via the inductive element 114 and rectifier 442 of the sensor 100. In some non-limiting embodiments, the power switch 464 may switch components of the sensor 100 from being powered by the voltage VSUP produced by the rectifier 442 using a current induced in the inductive element 114 to being powered by the voltage VBAT produced by the charge storage device 107.

In some embodiments, the power switch 464 may switch the sensor 100 to power itself from the power of the on-board charge storage device 107 in response to an autonomous measurement command initiated by the measurement scheduler 328. For instance, in some embodiments, the sensor 100 may be in a sleep mode while the sensor 100 is not receiving power from an external device 101. In the sleep mode, no power would be supplied to one or more of the I/O digital circuitry 336, command decoder 322, memory 324, measurement controller 320, and analog interface 318. However, in the sleep mode, at least the clock 330 and measurement scheduler 328 would receive power from the charge storage device 107. The measurement scheduler 328 may use the CSD-powered clock 330 to determine when to initiate an autonomous measurement. In some embodiments, in response to an autonomous measurement command from the measurement scheduler 328, the power switch 464 may switch the sensor 100 to the power of the charge storage device 107. In some embodiments, one or more of the I/O digital circuitry 336, command decoder 322, memory 324, measurement controller 320, and analog interface 318 would then be powered by the charge storage device 107. In some non-limiting embodiments, when the sensor 100 is switched to the power of the charge storage device 107, the voltage VBAT (instead of the voltage VSUP) may be used to produce the voltage (e.g., voltages VDDA, VDDD, and VLED) that powers the sensor 100. In this way, the measurement scheduler 328 can wake up the sensor 100 by issuing a measurement command that causes the power switch 464 to switch the sensor 100 to the power of the charge storage device 107.

In some embodiments, as shown in FIG. 4A, the I/O analog circuitry 336 may include a CSD monitor 466 configured to monitor the voltage VBAT produced by the charge storage device 107 and provide feedback about the charge level of the charge storage device 107. For instance, in some non-limiting embodiments, the CSD monitor 466 may indicate whether the voltage VBAT is sufficient for sensor operation, and the power switch 464 may only switch the sensor 100 to CSD power if the CSD monitor 466 indicates that the voltage VBAT is sufficient for sensor operation. In some non-limiting embodiments, the CSD monitor 466 may determine whether the voltage VBAT is sufficient for sensor operation by comparing the voltage VBAT to an operational threshold voltage. In some non-limiting embodiments, the CSD monitor 466 may indicate whether the charge storage device 107 is fully charged, and the CSD charger 456 may be configured to stop charging the charge storage device 107 when the charge storage device 107 is fully charged. In some non-limiting embodiments, the CSD monitor 466 may determine whether the charge storage device 107 is fully charged by comparing the voltage VBAT to a fully-charged threshold voltage. In some non-limiting embodiments, the measurement scheduler 328 may adjust the frequency at which autonomous measurements are taken based on the charge level of the charge storage device 107 as indicated by the CSD monitor 466. For instance, in one non-limiting embodiment, if the CSD monitor 466 indicates that the charge level of the charge storage device 107 is low, the measurement scheduler 328 may adjust the frequency at which autonomous measurements are taken.

In some embodiments, as shown in FIG. 4A, an I/O digital circuitry 334 may include one or more of a decoder 470, encoder 472, and protocol state machine 474. The decoder 470 may decode the data extracted by the data extractor 444 from the alternating current produced by inductive element 114. The command decoder 322 may receive the data decoded by the decoder 322 and may decode commands therefrom. In some non-limiting embodiments, the command decoder 322 may comprise a status register. In some embodiments, the encoder 472 may receive data from the command decoder 322 and encode the data. In some embodiments, the decoder 470 and encoder 472 may decode and encode the data in accordance with a communication protocol (e.g., Manchester or 8B/10B) as specified by a protocol state machine 474. In some non-limiting embodiments, the I/O digital circuitry 336 may include two or more sets of encoders and decoders with each set having its own protocol state machine. In this way, the sensor 100 may be able to convey and receive information using more than one communication protocol.

In some embodiments, as shown in FIG. 4A, the clamp/modulator 440 of the I/O analog circuitry 336 may receive the data encoded by the encoder 472 and may modulate the current flowing through the inductive element 114 as a function of the encoded data. In this way, the encoded data may be conveyed wirelessly by the inductive element 114 as a modulated electromagnetic wave. The conveyed data may be detected by an external reading device 101 by, for example, measuring the current induced by the modulated electromagnetic wave in a coil of the external reading device. Furthermore, by modulating the current flowing through the inductive element 114 as a function of the encoded data, the encoded data may be conveyed wirelessly by the inductive element 114 as a modulated electromagnetic wave even while the inductive element 114 is being used to produce operating power for the sensor 100. In some non-limiting embodiments, the communications received by the inductive element 114 and/or the communications conveyed by the inductive element 114 may be radio frequency (RF) communications. Although, in the illustrated embodiments, the sensor 100 includes a single inductive element 114, some alternative embodiments of the sensor 100 may include two or more inductive elements (e.g., one coil for data conveyance and one coil for power and data reception).

In some embodiments, the memory 324 may be a nonvolatile storage medium. In some non-limiting embodiments, the memory 324 may be an electrically erasable programmable read only memory (EEPROM). However, in some alternative embodiments, other types of nonvolatile storage media, such as flash memory, may be used. In some embodiments, the memory 324 may be a 20 by 1024 bit memory, but this is not required, and, in some alternative embodiments, the memory 324 may be a different size. In some non-limiting embodiments, the memory 324 may include an address decoder. In some embodiments, the memory 324 may store measurement information autonomously generated while the sensor 100 is powered from and on-site charge storage device (e.g., charge storage device 107) and/or measurement information generated in response to a measurement command received from an external device 101 while the sensor 100 is receiving power from the external device 101. In some embodiments, the memory 324 may additionally or alternatively store one or more timestamps identifying when the measurement data was generated, sensor calibration data, a unique sensor identification, setup information, and/or integrated circuit calibration data. In some non-limiting embodiments, the unique identification information may, for example, enable full traceability of the sensor 100 through its production and subsequent use. In some embodiments, the memory 324 may receive write data (i.e., data to be written to the memory 324) from the command decoder 322 and may supply read data (i.e., data read from the memory 324) to the command decoder 322. In some non-limiting embodiments, memory 324 may have an integrated charge pump and/or may be connected to an external charge pump.

In some embodiments, as shown in FIG. 4B, the analog interface 318 may include a current source 478, one or more light source drivers 480, an analog to digital converter (ADC) 482, a signal multiplexer (MUX) 484, a comparator 486, one or more photodetectors 488 (e.g., photodetectors 224 and 226), and/or one or more temperature transducers 490 and 492. In some non-limiting embodiments, the comparator 486 may be a transimpedance amplifier (TIA). However, this is not required, and, in some alternative embodiments, the comparator 486 may be a different type of comparator. In a non-limiting embodiment, one or more of the temperature transducers 490 and 492 may be a band-gap based temperature transducer. However, in some alternative embodiments, different types of temperature transducers may be used, such as, for example, thermistors or resistance temperature detectors. In some non-limiting embodiments, the analog interface 318 may include two temperature transducers 490 and 492 for high reliability operation and for detection of temperature error/failure with higher probability. In some non-limiting embodiments, the second temperature transducer 492 may be a redundant temperature transducer that is the same as the first temperature transducer 490 and may be for temperature plausibility/diagnostic purposes. In some embodiments, the one or more temperature transducers 490 and 492 may be fabricated in the substrate 116 or mounted on the semiconductor substrate 116. The one or more temperature transducers 490 and 492 may output an analog temperature measurement signal indicative of the temperature of the sensor 100.

In some embodiments, as shown in FIG. 4B, the one or more photodetectors 488 may be fabricated in or mounted on the substrate 116. In some embodiments, the one or more photodetectors 488 may include a photodetector array including, for example, eight photodetectors. In some non-limiting embodiments, the one or more photodetectors may be interdigitated. In some non-limiting embodiments, one or more of the photodetectors may have optimized ultraviolet sensitivity. In some non-limiting embodiments having multiple photodetectors, the photodetectors 488 may be freely allocated as signal photodetectors (e.g., photodetector 224) or as reference photodetectors (e.g., photodetector 226). In some non-limiting embodiments, one or more of the photodetectors 488 may be coated with one or more optical filters. In some embodiments, the substrate 116 may include one or more contacts, such as, for example, contacts PDEXT1, PDEXT2, PDEXT3, and PDEXT4, for electrically connecting one or more photodetectors that are external to the substrate 116. The one or more exterior photodetector contacts may be connected to photodetector input circuitry 494, which may, for example, amplify the exterior photodetector inputs and/or provide other signal processing.

In some embodiments, the one or more light source drivers 480 may drive the one or more light sources 108 using current provided by the current source 478. In some embodiments, the one or more light sources 108 of the sensor 100 may include a first light source (e.g., a UV light source) and a second light source (e.g., a blue light source). In some embodiments, the one or more light source drivers 480 may include a first light source driver 496 for driving the first light source and a second light source driver 498 for driving the second light source. In some embodiments, as illustrated in FIG. 4B, the first and second light sources may be mounted to the substrate 116 and connected to the substrate 116 via contacts LED1C and LED2C. However, this is not required, and, in some alternative embodiments, one or more of the first and second light sources may be fabricated in the substrate 116. In some non-limiting embodiments, the one or more light source drivers 480 may include one or more exterior light sources drivers 402 and 404 for driving one or more exterior light sources (i.e., one or more light sources of the sensor 100 that are not mounted on or fabricated in the substrate 116). In some non-limiting embodiments, the one or more light sources may be powered using a voltage VLED generated using the charge pump 450. In some embodiments, the one or more light source drivers 480 may receive a light source selection signal from the measurement controller 320 that identifies which of the one or more light sources 108 should be driven by the one or more light source drivers 480.

In some embodiments, the current source 478 may receive a signal from the measurement controller 320 indicating the light source current at which a light source 108 is to be driven, and the current source 478 may provide a current accordingly. The one or more light sources 108 may emit radiation from an emission point in accordance with one or more drive signals from the one or more light source drivers 480. The radiation may excite one or more indicator molecules 104 distributed in one or more analyte indicators 106 on at least a portion of the exterior surface of the sensor housing 102. The one or more photodetectors 488 (e.g., first and second photodetectors 224 and 226) may each output an analog light measurement signal indicative of the amount of light received by the photodetector. For instance, the first photodetector 224 may output a first analog light measurement signal indicative of the amount of light received by the first photodetector 224, and the second photodetector 226 may output a first analog light measurement signal indicative of the amount of light received by the second photodetector 226.

In some embodiments, as shown in FIG. 4B, the analog interface 318 may include an input multiplexor 406. The input multiplexor 406 may receive the analog light measurement signals outputted by the one or more photodetectors 488 and by any external photodetectors. In some embodiments, under the control of the measurement controller 320, the input multiplexor 406 may select one or two of the analog light measurement signals to pass through to the comparator 486. In some embodiments, the comparator 486 may amplify and/or compare the one or more analog light measurement signals received from the input multiplexor 406. For instance, in some non-limiting embodiments, the input multiplexor 406 may select the first and second analog light measurement signals from the first and second photodetectors 224 and 226, respectively, and output an analog light difference measurement signal indicative of the difference between the first and second analog light measurement signals.

In some embodiments, as shown in FIG. 4B, the analog interface 318 may include a sample and hold (S&H) measurement circuit 408. The S&H measurement circuit 408 may receive one or more of the analog light measurement signals or the analog light difference measurement signal and provide a short-term measurement (e.g., a sample of the effective photo current shortly after a respective light source 108 has been switched off). In some non-limiting embodiments, the analyte monitoring system may use this measure to analyze the dynamic phosphorescence of the analyte indicator 106 in order to determine aging effects.

In some embodiments, as shown in FIG. 4B, the signal MUX 484 may receive one or more analog temperature measurement signals from the one or more temperature transducers 490 and 492, one or more analog light measurement signals from the one or more photodetectors 488 (and/or from any external photodetectors), an analog light difference measurement signal from the comparator 486, and/or one or more analog short term measurements from the S&H measurement circuit 408. In some embodiments, under the control of the measurement controller 320, the signal MUX 484 may select one of the received signals and output the selected signal to the ADC 482. The ADC 482 may receive the selected analog signal from the signal MUX 484, convert the received analog signal to a digital signal, and supply the digital signal to the measurement controller 320. In this way, the ADC 482 may convert the one or more analog temperature measurement signals, the one or more analog light measurement signals, the analog light difference measurement signal, and/or the one or more analog short term measurements to one or more digital temperature measurement signals, one or more digital light measurement signals, a digital light difference measurement signal, and/or one or more analog short term measurements, respectively. In some embodiments, the ADC 482 may supply the digital signals, one at a time, to the measurement controller 320. In some non-limiting embodiments, the ADC 482 may be a 16 bit ADC, and the ADC 482 may have, for example, a 2 ms conversion time. However, this is not required, and some alternative embodiments may use a different ADC.

In some non-limiting embodiments, the circuitry of sensor 100 may include a field strength measurement circuit. In some embodiments, the field strength measurement circuit may be part of the I/O analog circuitry 336, I/O digital circuitry 334, or the measurement controller 320, or the field strength measurement circuit may be a separate functional component. The field strength measurement circuit may measure the received (i.e., coupled) power (e.g., in mWatts). The field strength measurement circuit of the sensor 100 may produce a coupling value proportional to the strength of coupling between the inductive element 114 of the sensor 100 and an inductive element 103 of an external device 101. For example, in non-limiting embodiments, the coupling value may be a current or frequency proportional to the strength of coupling.

In some non-limiting embodiments, as illustrated in FIG. 4A, the clamp/modulator 440 of the I/O analog circuitry 336 acts as the field strength measurement circuit by providing a value (e.g., $I_{couple}$) proportional to the field strength. As illustrated in FIG. 4B, the field strength value $I_{couple}$ may be provided as an input to the signal MUX 484 (e.g., via the input MUX 406). When selected, the signal MUX 484 may output the field strength value $I_{couple}$ to the ADC 482. The ADC 482 may convert the field strength value $I_{couple}$ received from the signal MUX 484 to a digital field strength value signal and supply the digital field strength signal to the measurement controller 320. In this way, the field strength measurement may be made available to the measurement controller 320 (e.g., for determining whether the field strength is sufficient to carry out a measurement command received from an external device 101 or for use in initiating an analyte measurement command trigger based on dynamic field alignment).

In some embodiments, as shown in FIG. 4A, a test interface 476 may be mounted on or fabricated in the substrate 116. In some embodiments, the test interface 476 may enable wafer-level production testing of the substrate 116. In some non-limiting embodiments, the test interface 476 may be an SPI-taped interface (i.e., a wireless communication interface). In some non-limiting embodiments, the test interface 476 may receive signals via one or more contacts and may output signals via one or more contacts. The test interface 476 may communicate with the measurement controller 320 via the command decoder 322.

Figure 5:
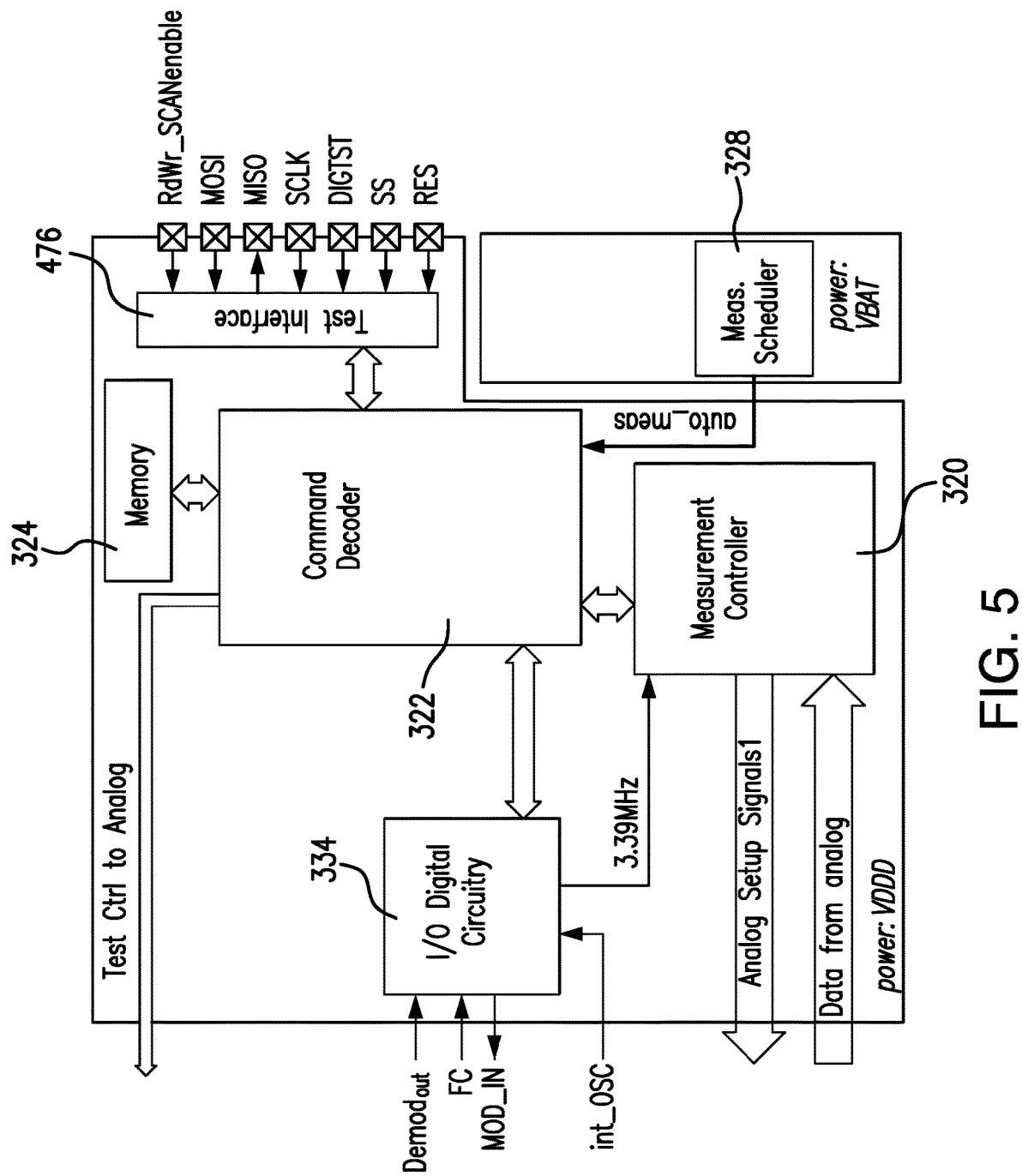
FIG. 5 is a block diagram illustrating the functional blocks of some of the circuitry mounted on or fabricated in the substrate of the sensor according to some embodiments.

FIG. 5 is a block diagram illustrating the functional blocks of some of the circuitry mounted on or fabricated in the substrate 116 according to some embodiments. In some embodiments, as shown in FIG. 5, one or more of the command decoder 322, address decoder of the memory 324, and test interface 476 may be part of the I/O digital circuitry 334.

In some embodiments, as shown in FIG. 5, the measurement scheduler 328 may issue an autonomous measurement command to the command decoder 322, which may decode the command and/or send the command to the measurement controller 320. The measurement controller 320 may control the sensor elements 332 of the analog interface 318 to perform an autonomous analyte measurement, and the results of the autonomous analyte measurement may be stored in the memory 324.

Figure 6:
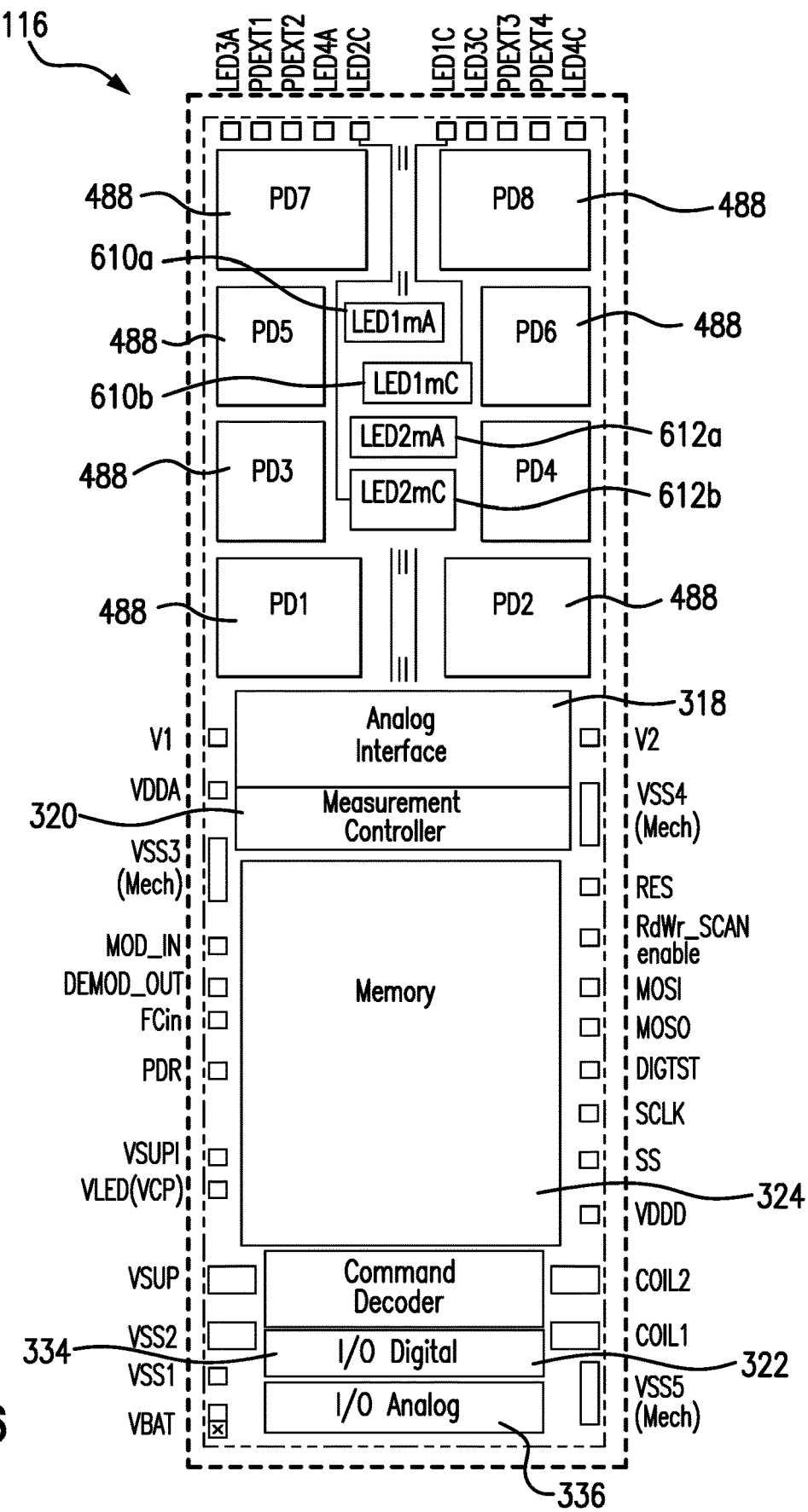
FIG. 6 illustrates the layout of a semiconductor substrate embodying aspects of the present invention.

FIG. 6 illustrates the layout of a substrate 116 according to a non-limiting embodiment of the present invention in which the substrate 116 is a semiconductor substrate. In some non-limiting embodiments, the substrate 116 may have a length of approximately 6010 μm and a width of approximately 1610 μm. However, this is not required, and, in some alternative embodiments, the substrate 116 may have a different length and/or a different width. In some embodiments, as shown in FIG. 6, eight photodetectors 488 (e.g., photodetectors 224 and 226) may be fabricated in the semiconductor substrate 116, and the substrate 116 may have light source mounting pads 610a, 610b, 612a, and 612b for mounting first and second light sources 108 (e.g., a UV light source and a blue light source). However, this is not required, and, in some alternative embodiments, the substrate 116 may have a different number of photodetectors 488 fabricated therein, the photodetectors 488 may be mounted on the substrate 116 instead of fabricated therein, the substrate may have a different number of light source mounting pads (e.g., mounting pads for one or three light sources), and/or the light sources 108 may be fabricated in the substrate 116 instead of mounted thereon. In some non-limiting embodiment, the light source mounting pads 610a, 610b, 612a, and 612b may connect to the anodes and cathodes of light sources 108 mounted on the substrate 116.

In some non-limiting embodiments, the photodetectors 488 may be symmetrically formed on each side of a center line of the substrate 116. In some embodiments, the light source mounting pads 610a, 610b, 612a, and 612b may be configured such that the emission points of light sources 108, when mounted on the light source mounting pads 610a, 610b, 612a, and 612b, are aligned on the center line running between the photodetectors 488. Similarly, in some embodiments in which the light sources 108 are fabricated in the substrate 116, the emission points of the fabricated light sources 108 are aligned on the center line running between the photodetectors 488. In some embodiments, the fabrication of symmetrical photodetectors 488 (i.e., photodetectors 488 which are symmetrical relative to the light source emission points) may realize dual channels that are closer to being identical to each other than can be achieved by using discrete parts (e.g., photodetectors mounted on the semiconductor substrate 116). The nearly identical photodetector channels may improve the accuracy of the sensor measurements. This may be especially true when, in some embodiments, the nearly identical dual photodetector channels are utilized as a signal channel and a reference channel, respectively.

In some embodiments, as illustrated in FIG. 6, the photodetectors 488 may surround the light source mounting pads 610a, 610b, 612a, and 612b. In some non-limiting embodiments, the photodetectors 488 above and below the light source mounting pads 610a, 610b, 612a, and 612b may be larger than the photodetectors 488 to the left and right of the light source mounting pads 610a, 610b, 612a, and 612b. However, this is not required, and, in some alternative embodiments, all of the photodetectors 488 may have the same size.

The layout of the photodetectors 488 on silicon substrate 116 is not limited to the embodiment illustrated in FIG. 6. One or more alternative embodiments may use different photodetector layouts.

Figure 7:
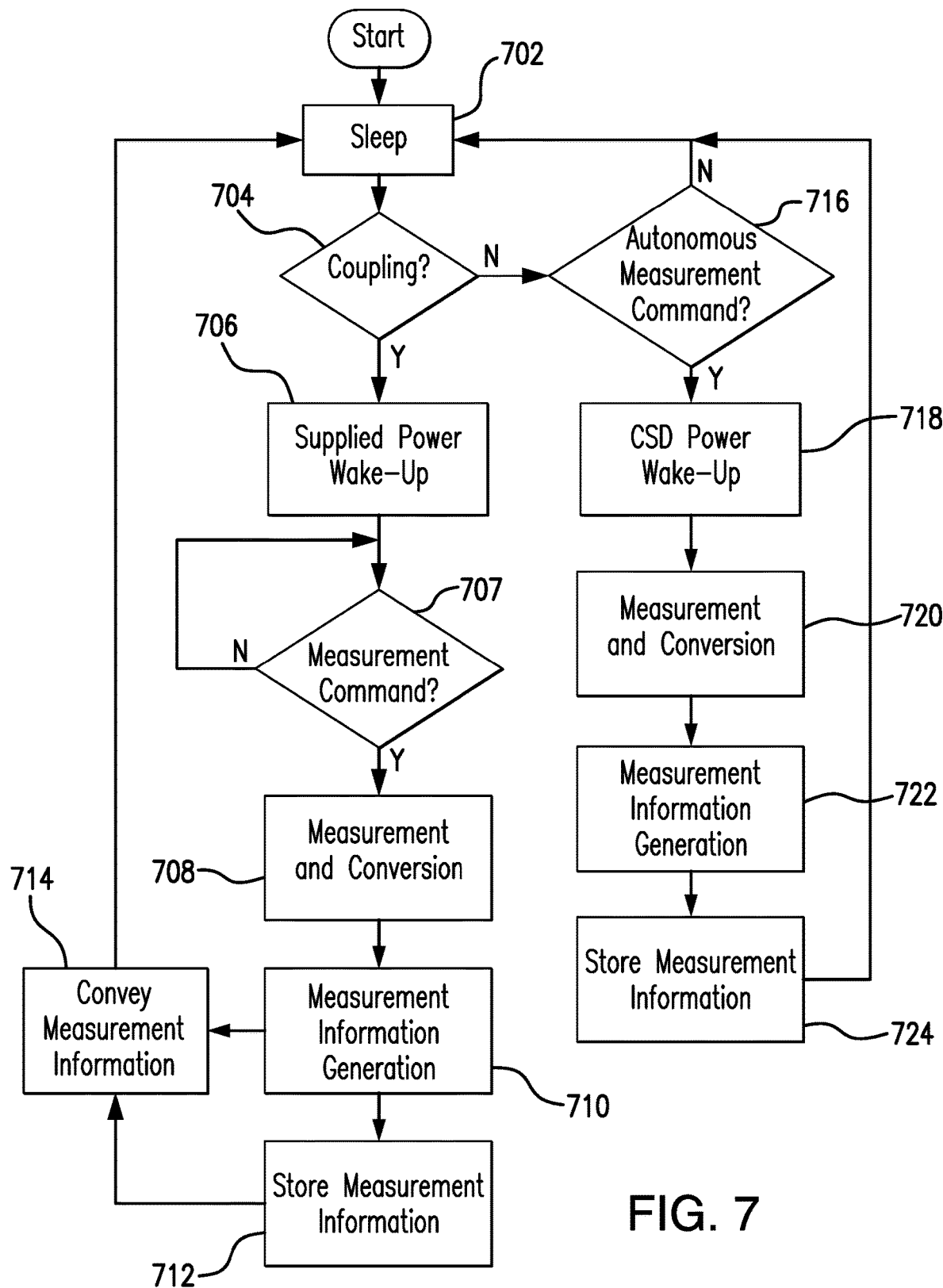
FIG. 7 is a flow chart illustrating an exemplary sensor control process that may be performed by an analyte sensor embodying aspects of the present invention.

FIG. 7 is a flow chart illustrating a non-limiting embodiment of a sensor control process that may be performed by the analyte sensor 100. In some embodiments, the sensor control process may begin with a step 702 in which the sensor 100 enters a sleep (i.e., dormant) mode. In some embodiments, in the sleep mode, no power is supplied to one or more of the I/O digital circuitry 336, command decoder 322, memory 324, measurement controller 320, and analog interface 318, but at least the clock 330 and measurement scheduler 328 are powered by the charge storage device 107.

In some embodiments, the sensor control process may include a step 704 of supplying power to the sensor 100 by coupling the inductive element 103 of the external device 101 and the inductive element 114 of the sensor 100 within an electrodynamic field. If power is supplied to the sensor 100 (i.e., if the inductive elements 103 and 114 are coupled within an electrodynamic field), the sensor control process may proceed to a step 706. However, if no power (or insufficient power) is supplied to the sensor 100, the sensor control process may proceed to a step 716.

In some embodiments, the sensor control process may include a step 706 of waking-up/activating the sensor 100 using power supplied by an external device 101. In some embodiments, the supplied power wake-up step 706 may include using the electrodynamic field to generate operational power. In some non-limiting embodiments, the electrodynamic field may induce a current in inductive element 114 of sensor 100, and the input/output (I/O) analog circuitry 336 may convert the induced current into power for operating the sensor 100. In some non-limiting embodiments, the rectifier 442 may convert an alternating current produced by the inductive element 114 to a direct current that may be used to power the sensor 100. In some non-limiting embodiments, the rectifier 442 may supply a voltage VSUP, and the I/O analog circuitry 336 may use the voltage VSUP to produce one or more voltages, such as, for example, voltage VDDA, which may be used to power the analog interface 318; voltage VLED, which may be used to power the one or more light sources 108; and voltage VDDD, which may be used to power one or more of the I/O digital circuit 336, the memory 324, the measurement controller 320, the command decoder 322, the measurement scheduler 318, and the test interface 476.

In some embodiments, the sensor control process may include a step 707 in which the sensor 100 determines whether a command has been decoded (e.g., from modulation of the electrodynamic field). In some non-limiting embodiments, the data extractor 444 may extract data from the current induced in inductive element 114, the decoder 470 may decode the extracted data, and the command decoder 322 may decode one or more commands (e.g., a measurement command) from the decoded extracted data. The command decoder 322 may send a decoded command to the measurement controller 320. In some embodiments, the one or more commands and power received by the sensor 100 may be received from the external device 101.

If a measurement command has not been decoded, the sensor control process may return to step 707 until a measurement command is received (assuming power continues to be supplied to the sensor 100). If a measurement command has been decoded, the sensor control process may proceed to steps 708, 710, 712, and 714 for execution of the measurement command. In some embodiments, the sensor 100 may execute the decoded measurement command under control of the measurement controller 320.

In some embodiments, the sensor control process may include a step 708 in which the sensor 100 performs a measurement and conversion process. The measurement and conversion process may, for example, be performed by the analog interface 318 under control of the measurement controller 320. In some embodiments, the measurement and conversion sequence may include generating one or more analog measurements (e.g., using one or more of temperature transducers 488 and 490, one or more of light sources 108, one or more of photodetectors 480, one or more external photodetectors, the S&H measurement circuit 408, and/or comparator 486) and converting the one or more of the analog measurements to one or more digital measurements (e.g., using ADC 482). One example of the measurement conversion process that may be performed in step 708 is described with reference to FIG. 18 in U.S. Patent Application Publication No. 2013/0241745, which is incorporated by reference herein in its entirety.

In some embodiments, the sensor control process may include a step 710 in which the sensor 100 may generate measurement information in accordance with the one or more digital measurements produced during the measurement and conversion sequence performed in step 708. Depending on the one or more digital measurements produced in step 710, the measurement information may be indicative of the amount of an analyte in a medium in which the sensor 100 is implanted. In some embodiments, in step 710, the measurement controller 320 may receive the one or more digital measurements and generate the measurement information. In some embodiments, the measurement information may include a time-stamp identifying the time at which the analyte measurement was taken.

In some embodiments, the sensor control process may include a step 712 in which the sensor 100 stores the measurement information. In some embodiments, the measurement controller 320 may output the analyte measurement information to the command decoder 322, which may transfer the analyte measurement information to the memory 324. The memory 324 may save the received analyte measurement information. In some embodiments, the measurement controller 320 or command decoder 322 identify an address at which the measurement information is to be saved in the memory 324. In some non-limiting embodiments, the memory 324 may be configured as a first-in-first-out (FIFO) or last-in-first-out (LIFO) memory.

In some embodiments, the sensor control process may include a step 714 in which the sensor 100 conveys the analyte measurement information. In some embodiments, the sensor control process may proceed to step 714 after storing the measurement information in step 712. However, this is not required, and, in some alternative embodiments, the sensor control process may proceed to step 714 directly from step 710 in which the measurement information was generated. In some embodiments, the command decoder 322 may transfer the measurement information generated by the measurement controller 320 to the encoder 472. The encoder 472 may encode the measurement information. The clamp/modulator 442 may modulate the current flowing through the inductive element 114 as a function of the encoded measurement information. In this way, the encoded measurement information may be conveyed wirelessly by the inductive element 114 as a modulated electromagnetic wave.

In some embodiments, the encoded measurement information wirelessly conveyed by the sensor 100 may be received by an external device 101.

In some embodiments, in step 714, the sensor 100 may convey stored measurement information generated from one or more previous analyte measurements in addition to conveying the measurement information generated from the most recent analyte measurement. In some non-limiting embodiments, the sensor 100 may convey stored measurement information generated from a set number (e.g., five, ten, twenty, or one hundred) of previous analyte measurements in addition to the most recent analyte measurement. However, this is not required, and, in some alternative embodiments, the sensor 100 may convey all of the stored measurement information that was generated within a set period of time (e.g., all of the stored measurement information that was generated within the last one minute, five minutes, half hour, hour, four hours, twelve hours, day, or week). In some non-limiting embodiments, the stored measurement information may be accessed from the memory 324. In some non-limiting embodiments, the command decoder 322 may transfer the stored measurement information retrieved from the memory 324 to the encoder 472. The encoder 472 may encode the stored measurement information. The clamp/modulator 442 may modulate the current flowing through the inductive element 114 as a function of the encoded stored measurement information. In this way, the encoded stored measurement information may be conveyed wirelessly by the inductive element 114 as a modulated electromagnetic wave. In some embodiments, the encoded stored measurement information wirelessly conveyed by the sensor 100 may be received by an external device 101. In some embodiments, conveying measurement information from one or more previous analyte readings in addition to the current reading may enable the external device 101 to produce analyte trend information.

In some embodiments, the sensor 100 may be capable of executing other commands received by the sensor 100. For example, if command decoder 322 decodes a retrieve stored measurement information command in step 707, the sensor control process may proceed directly to step 714, where the sensor 100 conveys stored measurement information from one or more previous analyte measurements without generating a new analyte measurement. In some non-limiting embodiments, the sensor 100 may execute a retrieve stored measurement information command by using the get result command execution process 1900 described with reference to FIG. 19 in U.S. Patent Application Publication No. 2013/0241745, which is incorporated by reference herein in its entirety.

In some embodiments, the sensor control process may include a step 716 in which the sensor 100 determines whether to perform an autonomous measurement. In some embodiments, the sensor 100 may perform step 716 while the sensor 100 is in sleep mode if no power (or insufficient power) is supplied to the sensor 100 (see steps 702 and 704). In some embodiments, the CSD-powered measurement scheduler 328 may determine whether to perform an autonomous measurement based on the continuous clock output of the CSD-powered clock 330. The measurement scheduler 328 may use the continuous clock output to keep track of time and may issue an autonomous measurement command when appropriate (e.g., at periodic intervals). If no autonomous measurement command has been issued, the sensor control process may proceed back to step 702. If an autonomous measurement command has been issued, the sensor control process may proceed to step 718.

In some embodiments, the sensor control process may include a step 718 of waking-up/activating the sleeping/dormant sensor 100 using power supplied by the charge storage device 107. In some embodiments, the CSD power wake-up step 718 may include using the power switch 464 to switch the sensor 100 from externally supplied power to CSD power. In some non-limiting embodiments, in response to an autonomous measurement command, the power switch 464 may switch components of the sensor 100 from being powered by the voltage VSUP produced by the rectifier 442 using a current induced in the inductive element 114 to being powered by the voltage VBAT produced by the charge storage device 107. In some embodiments, after the power switch 464 switches the sensor 100 to CSD power, one or more of the I/O digital circuitry 336, command decoder 322, memory 324, measurement controller 320, and analog interface 318 would then be powered by the charge storage device 107.

In some embodiments, after performing the CSD power sensor wake-up in step 718, the sensor control process may proceed to steps 720, 722, and 724 for execution of the autonomous measurement command. In some embodiments, in step 720, the sensor 100 may perform a measurement and conversion process. In some embodiments, in step 722, the sensor 100 may generate measurement information in accordance with the one or more digital measurements produced during the measurement and conversion sequence performed in step 720. In some embodiments, in step 724, the sensor 100 may store the measurement information. In some non-limiting embodiments, the steps 720, 722, and 724 may be similar to steps 708, 710, and 712, respectively, except that steps 720, 722, and 724 may be performed with one or more of the I/O digital circuitry 336, command decoder 322, memory 324, measurement controller 320, and analog interface 318 powered by the charge storage device 107 (instead of being powered by current induced in the inductive element 114 and rectified by the rectifier 442).

In some embodiments, after completion of steps 720, 722, and 724, the power switch 464 may switch the sensor 100 from CSD power to externally supplied power. If there is no externally supplied power (i.e., if the inductive elements 114 and 103 are not coupled within an electrodynamic field), the sensor control process may return to sleep mode. In some non-limiting embodiments, the measurement information stored in step 724 during execution of an autonomous measurement command may later be conveyed from the sensor 100 (e.g., in step 714) at a time when the inductive element 114 of the sensor is coupled with the inductive element 103 of an external device 101 in an electrodynamic field generated by the external device 101.

In some embodiments, the sensor 100 may operate in low and high RF field situations while powered by the charge storage device 107. In some embodiments, the low RF field situation occurs when the electrodynamic field is not strong enough to power a full sensor measurement. In some non-limiting embodiments, in a low RF field situation, the charge storage device 107 may power the sensor 100 or supplement the power provided by the weak electrodynamic field. In some embodiments, the high RF field situation occurs when the electrodynamic field is strong enough to power a full sensor measurement. In some non-limiting embodiments, in a high RF field situation, the charge storage device 107 and/or the high RF field may power the sensor 100.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention. For example, circuitry of the sensor 100 may be implemented in hardware, software, or a combination of hardware or software. The software may be implemented as computer executable instructions that, when executed by a processor, cause the processor to perform one or more functions.

For another example, in some alternative embodiments, the sensor 100 may not include a charge storage device 107. In these alternative embodiments, the sensor 100 may require externally supplied power for operation (e.g., power from an external device 101 placed in the proximity of the sensor 100 to provide power and data link to the sensor 100).

In some alternative embodiments, instead of determining whether a measurement command has been decoded in step 707, the sensor 100 may determine whether the strength of the electrodynamic field received by the sensor 100 is sufficient or insufficient for the sensor 100 to perform the analyte measurement and conversion, measurement information generation, measurement information storage, and measurement information conveyance of steps 708, 710, 712, and 714, respectively. If the strength of the electrodynamic field is sufficient, the sensor control process may proceed to steps 708, 710, 712, and 714. In some non-limiting embodiments, circuitry of the sensor 100 may produce a coupling value proportional to the strength of the coupling of the inductive element 103 of an external device 101 and the inductive element 114 of the sensor 100. In some non-limiting embodiments, the clamp/modulator 440 of the I/O analog circuitry 336 may produce a coupling value (e.g., $I_{couple}$) proportional to the received field strength based on the current induced in the inductive element 114 by the electrodynamic field. In one non-limiting embodiment, the coupling value proportional to the field strength may be converted (e.g., by ADC 664) to a digital coupling value proportional to the received field strength. In some non-limiting embodiments, the sensor 100 may use the analog and/or digital coupling value to determine whether the strength of the electrodynamic field received by the sensor 100 is sufficient for the sensor 100 to perform an analyte measurement. For instance, in one non-limiting embodiment, the measurement controller 532 may compare the digital coupling value to an analyte measurement field strength sufficiency threshold and produce an indication that the strength of the electrodynamic field received by the sensor is either sufficient or insufficient for the implanted sensor to perform the analyte measurement.

In some alternative embodiments, the sensor 100 may perform one or more of steps 708, 710, 712, and 714 with the sensor operating under charge storage device power (e.g., if the current induced in the inductive element 114 is sufficient for data communication but insufficient to provide operational power for the sensor 100). In these alternative embodiments, the sensor 100 may perform a measurement operation initiated by an external device 101 with operational power for the measurement operation being provided by the charge storage device 107.

What is claimed is:

1. A method of using a sensor to measure an analyte in a medium within a living animal, the method comprising:
   controlling sensor elements of the sensor to generate a first analyte measurement signal using power provided by an electrodynamic field generated by an external device while an inductive element of the sensor is in the electrodynamic field generated by the external device, wherein the sensor elements are configured to generate the first analyte measurement signal based on a detectable property exhibited by an analyte indicator of the sensor, and the analyte indicator is configured to exhibit the detectable property based on the amount or concentration of the analyte in the medium;

generating first measurement information based on the first analyte measurement signal;

controlling an input/output circuit of the sensor to wirelessly convey the first measurement information to the external device via the inductive element while the inductive element is in the electrodynamic field generated by the external device;

using a power switch to switch at least the sensor elements from being powered by the electrodynamic field to being powered by a charge storage device of the sensor;

controlling the sensor elements of the sensor to generate a second analyte measurement signal using power provided by the charge storage device while the inductive element of the sensor is not in the electrodynamic field generated by the external device, wherein the sensor elements are configured to generate the second analyte measurement signal based on a detectable property exhibited by the analyte indicator of the sensor;

generating second measurement information based on the second analyte measurement signal;

storing the second measurement information in a non-volatile storage medium of the sensor; and controlling the input/output circuit of the sensor to wirelessly convey the stored second measurement information to the external device via the inductive element while the inductive element is in the electrodynamic field generated by the external device.

2. The method of claim 1, further comprising:

using a measurement scheduler that is powered by the charge storage device to periodically determine that an interval of time has passed based on the output of a clock that is powered by the charge storage device; and wherein switching at least the sensor elements from being powered by the electrodynamic field to being powered by the charge storage device is in response to a determination that the interval of time has passed.

3. A sensor comprising:

an analyte indicator configured to exhibit a detectable property based on the amount or concentration of an analyte in a medium within a living animal;

sensor elements configured to generate an analyte measurement signal based on the detectable property exhibited by the analyte indicator;

an inductive element configured to produce a current when in an electrodynamic field generated by an external device;

an input/output circuit;

a measurement controller;

a non-volatile storage medium;

a charge storage device;

a clock that is powered by the charge storage device; and a measurement scheduler that is powered by the charge storage device and is configured to use an output of the clock to periodically determine that an interval of time has passed;

wherein the measurement controller is configured to, in response to a determination that the interval of time has passed:
  (i) control the sensor elements to generate an analyte measurement signal using power provided by the charge storage device;
  (ii) generate measurement information based on the analyte measurement signal; and
  (iii) store the measurement information in the non-volatile storage medium;

wherein the input/output circuit is configured to wirelessly convey the measurement information to the external device via the inductive element; and wherein the measurement controller is further configured to control the input/output circuit to wirelessly convey the measurement information to the external device while the inductive element is in the electrodynamic field generated by the external device.

4. A sensor comprising:

an analyte indicator configured to exhibit a detectable property based on the amount or concentration of an analyte in a medium within a living animal;

sensor elements configured to generate an analyte measurement signal based on the detectable property exhibited by the analyte indicator;

a measurement controller;

a non-volatile storage medium;

a charge storage device;

a clock that is powered by the charge storage device;

a measurement scheduler that is powered by the charge storage device and is configured to use an output of the clock to periodically determine that an interval of time has passed; and a power switch;

wherein the measurement controller is configured to, in response to a determination that the interval of time has passed:
  (i) control the sensor elements to generate an analyte measurement signal using power provided by the charge storage device;
  (ii) generate measurement information based on the analyte measurement signal; and
  (iii) store the measurement information in the non-volatile storage medium;

wherein the power switch is configured to switch one or more of the sensor elements and the measurement controller from being powered by an external device to being powered by the charge storage device in response to the determination that the interval of time has passed.

5. A method of using a sensor to measure an analyte in a medium within a living animal, the method comprising:

using a charge storage device of the sensor to power a measurement scheduler and a clock;

using the measurement scheduler to periodically determine that an interval of time has passed based on an output of the clock;

controlling sensor elements of the sensor to generate an analyte measurement signal using power provided by the charge storage device in response to a determination that the interval of time has passed, wherein the analyte measurement signal is based on a detectable property exhibited by an analyte indicator of the sensor, and the analyte indicator is configured to exhibit the detectable property based on the amount or concentration of the analyte in the medium;

generating measurement information based on the analyte measurement signal;

storing the measurement information in a non-volatile storage medium of the sensor; and controlling an input/output circuit to wirelessly convey the measurement information to an external device via an inductive element while the inductive element is in an electrodynamic field generated by the external device.

6. A method using a sensor to measure an analyte in a medium within a living animal, the method comprising:
- using a charge storage device of the sensor to power a measurement scheduler and a clock;
- using the measurement scheduler to periodically determine that an interval of time has passed based on an output of the clock;
- controlling sensor elements of the sensor to generate an analyte measurement signal using power provided by the charge storage device in response to a determination that the interval of time has passed, wherein the analyte measurement signal is based on a detectable property exhibited by an analyte indicator of the sensor, and the analyte indicator is configured to exhibit the detectable property based on the amount or concentration of the analyte in the medium;
- generating measurement information based on the analyte measurement signal;
- storing the measurement information in a non-volatile storage medium of the sensor; and
- switching the sensor elements of the sensor from being powered by an external device to being powered by the charge storage device in response to the determination that the interval of time has passed.

* * * * *